(12) United States Patent
Her

(10) Patent No.: US 11,478,617 B2
(45) Date of Patent: Oct. 25, 2022

(54) MEDICAL TUBE HOLDER

(71) Applicant: SMHERS, Paju-si (KR)

(72) Inventor: Se Hee Her, Seoul (KR)

(73) Assignee: SMHERS, Paju-si (KR)

( * ) Notice: Subject to any disclaimer, the term of this patent is extended or adjusted under 35 U.S.C. 154(b) by 0 days.

(21) Appl. No.: 16/982,768

(22) PCT Filed: Mar. 19, 2018

(86) PCT No.: PCT/KR2018/003152
§ 371 (c)(1),
(2) Date: Sep. 21, 2020

(87) PCT Pub. No.: WO2019/182167
PCT Pub. Date: Sep. 26, 2019

(65) Prior Publication Data
US 2021/0008346 A1 Jan. 14, 2021

(51) Int. Cl.
*A61M 25/01* (2006.01)
*A61M 25/02* (2006.01)

(52) U.S. Cl.
CPC ............ *A61M 25/02* (2013.01); *A61M 25/01* (2013.01); *A61M 25/0111* (2013.01)

(58) Field of Classification Search
CPC .. A61M 25/02; A61M 25/01; A61M 25/0111; A61M 39/16; A61M 39/165; A61M 39/18; A61M 39/162; A61M 2039/087; A61M 39/08; A61M 39/28; A61M 2025/0062; A61M 25/002; A61M 25/0113; A61J 1/035; B65D 5/2057
See application file for complete search history.

(56) References Cited

U.S. PATENT DOCUMENTS

| 3,345,988 | A | * | 10/1967 | Vitello | A61M 25/002 604/172 |
| 6,558,060 | B1 | * | 5/2003 | Raju | A61M 25/09 401/9 |
| 8,657,792 | B1 | * | 2/2014 | Hintze | A61M 5/14 604/174 |

(Continued)

FOREIGN PATENT DOCUMENTS

| CN | 102740924 A | 10/2012 |
| JP | 09-002531 A | 1/1997 |

(Continued)

*Primary Examiner* — Bhisma Mehta
*Assistant Examiner* — Phoebe Anne Staton
(74) *Attorney, Agent, or Firm* — Novick, Kim & Lee PLLC; Jae Youn Kim

(57) ABSTRACT

A medical tube holder is proposed. The medical tube holder includes: holder bodies and surrounding an outer surface of a medical tube; and fluid pockets provided in the holder bodies to form a predetermined space and discharge fluid stored therein to the outer surface of the medical tube while at least a part of the fluid pockets is broken when pressed by an external force. The fluid pockets are formed in the medical tube holder, and when the fluid pockets are pressed by the external force, the fluid pockets are broken and a fluid (i.e., a lubricant) stored therein is discharged to an outer surface of the medical tube. Accordingly, a user may easily apply the fluid such as the lubricant by using the medical tube holder.

7 Claims, 8 Drawing Sheets

(56) References Cited

U.S. PATENT DOCUMENTS

| | | | | |
|---|---|---|---|---|
| 8,926,204 B1* | 1/2015 | D'Ignazio | ............... | A47L 25/04 |
| | | | | 401/10 |
| 2005/0070882 A1 | 3/2005 | McBride | | |
| 2012/0165737 A1* | 6/2012 | Davis | .................... | A61M 39/18 |
| | | | | 604/179 |
| 2013/0327672 A1* | 12/2013 | Kurowski | ................. | B01L 3/52 |
| | | | | 206/462 |
| 2014/0060655 A1* | 3/2014 | Ramos | ................ | A61M 39/284 |
| | | | | 137/1 |
| 2019/0262583 A1 | 8/2019 | Her | | |

FOREIGN PATENT DOCUMENTS

| JP | 2009-125583 A | 6/2009 |
|---|---|---|
| JP | 2012-507318 A | 3/2012 |
| JP | 2013-503709 A | 2/2013 |
| KR | 20170131024 A | 11/2017 |
| KR | 10-2018-0029760 A | 3/2018 |
| WO | 03/008029 A2 | 1/2003 |
| WO | 2011/028898 A1 | 3/2011 |

* cited by examiner

MEDICAL TUBE HOLDER

TECHNICAL FIELD

The present disclosure relates to a medical tube holder and, more particularly, to a medical tube holder that enables a medical tube to be inserted into a patient's body or to be removed from the patients' body, while a user does not directly touch the tube by a hand, by surrounding an outer circumferential surface of the medical tube such as a catheter inserted into the patient's body.

BACKGROUND ART

A catheter is a kind of tube used for medical purposes, and is widely used as the name for a common tubular instrument. Catheters are of various materials, sizes, and shapes depending on their use. The use of catheters includes discharging of deposited residue in patient's body cavities or various organs, suctioning of perfusate for cleaning, measuring of cardiovascular dynamics or central venous pressure, and injecting of drugs or contrast agents into the patient's body.

Such a medical tube is usually made of biocompatible materials, and is designed long enough so as to be freely bent and enable an end of the medical tube to reach a desired area. Meanwhile, in order to insert the medical tube as described above into a patient's body, sterilized gloves must be put on first. The reason is that since the tube enters the patient's body, when hygiene management is not done thoroughly when inserting the tube, the patient may be infected with new germs, whereby disease of the patient may get worse. In particular, in the case of a patient with highly contagious disease such as AIDS, infection of the germs through the tube may have serious consequences.

Although the hygiene management is important when inserting a medical tube as described above, depending on medical staff, sometimes a treatment may be performed by touching the tube with non-sterile gloves or bare hands since wearing the requisite sterile gloves is cumbersome, time consuming, and is uncomfortable because of hands getting sweaty.

In order to solve this problem, Korean Patent No. 10-0451020 discloses a holder capable of holding a medical tube. By gripping the medical tube through such a holder, it is possible to prevent a user from having to use sterilization tweezers or directly holding the medical tube, thereby having the hygiene effect.

However, in the medical tube holder according to the related art, there is a disadvantage in that the medical tube holder may be applied only to a medical tube having a specific diameter, and a medical tube having a different diameter is unable to be used. Accordingly, in order to use the medical tube having a different standard, it is necessary to prepare a separate tube holder corresponding to the different standard.

Meanwhile, in many cases, medical lubricant jelly is applied to the outer circumferential surface of a medical tube so that the medical tube may be smoothly inserted into a patient's body, but convenience of use decreases because such applying of the lubricant requires additional work.

In addition, in a case of using a tube made of a hydrophilic material, water is used for lubrication, but since the case of using the tube also requires additional work, there occurs inconvenience.

DISCLOSURE

Technical Problem

The present disclosure is to solve the problems of the related art as described above, and an objective of the present disclosure is to provide a medical tube holder that may be used for medical tubes having various thicknesses.

Another objective of the present disclosure is to apply a lubricant to the outer surface of a medical tube by using a medical tube holder.

Technical Solution

According to the features of the present disclosure for achieving the above objectives, the present disclosure includes: a holder body surrounding an outer surface of a medical tube; and a fluid pocket provided on the holder body, the fluid pocket forming a predetermined space and discharging fluid stored therein to the outer surface of the medical tube, while at least a part of the fluid pocket is broken, when pressed by an external force.

The holder body may be configured as a thin plate shape, and the fluid pocket may be formed by a storage space formed by recessing a part of the holder body.

The fluid pocket may include: a storage space formed on the holder body; and a sealing film sealing the storage space and being configured to be broken by the internal pressure of the storage space when the external force is applied to the storage space.

The holder body may be composed of a first body and a second body capable of adjusting an interval therebetween, and the medical tube may be positioned between the first body and the second body.

Each of a first body and a second body of the holder body may be configured as a plate shape and be configured to be folded in a direction overlapping each other to surround the medical tube positioned therebetween, and the fluid pocket may be formed on at least one of the first body or the second body and protrudes toward an opposite direction of the medical tube.

The first body and the second body may be respectively provided with a fixing protrusion and a fixing groove formed at positions corresponding to each other to fix the first body and the second body in a folded and overlapped state to each other.

The first body or the second body may be provided with a fracture protrusion protruding toward an opposite body to break a sealing film of the opposite body in a process where the first body and the second body are in contact with each other, whereby the fluid in the storage space may be discharged therefrom.

A guide groove corresponding to the outer surface of the medical tube may be formed by being concaved in the holder body, and the guide groove may extend in an extension direction of the medical tube to surround the medical tube.

A through hole through which the medical tube passes may be formed inside the holder body, and the fluid pocket may protrude outwardly from the holder body.

The holder body may have a cylindrical shape, and a through hole of the holder body may have a circular cross section to correspond to the medical tube.

Advantageous Effects

The medical tube holder according to the present disclosure as described above has the following effects.

A fluid pocket is formed in a medical tube holder of the present disclosure, and when the fluid pocket is pressed by an external force, the fluid pocket is broken and a fluid (i.e., lubricant) stored therein is discharged to the outer surface of the medical tube. Accordingly, a user may easily apply the fluid such as the lubricant by using the medical tube holder, and since a separate work for applying the lubricant is unnecessary, there is an effect of improving work convenience.

In particular, since the present disclosure has a structure in which the fluid is distributed in a state of being stored in the sealed fluid pocket and is discharged as the fluid pocket is broken when to use, there is also an effect of having good storage ability for the fluid.

In addition, the medical tube holder of the present disclosure is composed of a first body and a second body, wherein the first and second bodies may be separated from each other or overlapped with each other so that medical tubes having various shapes and sizes may be positioned therebetween. Accordingly, since a single tube holder may be applicable to various medical tubes, there is an effect in that compatibility of the tube holder is improved.

MODE FOR INVENTION

Figure 1:
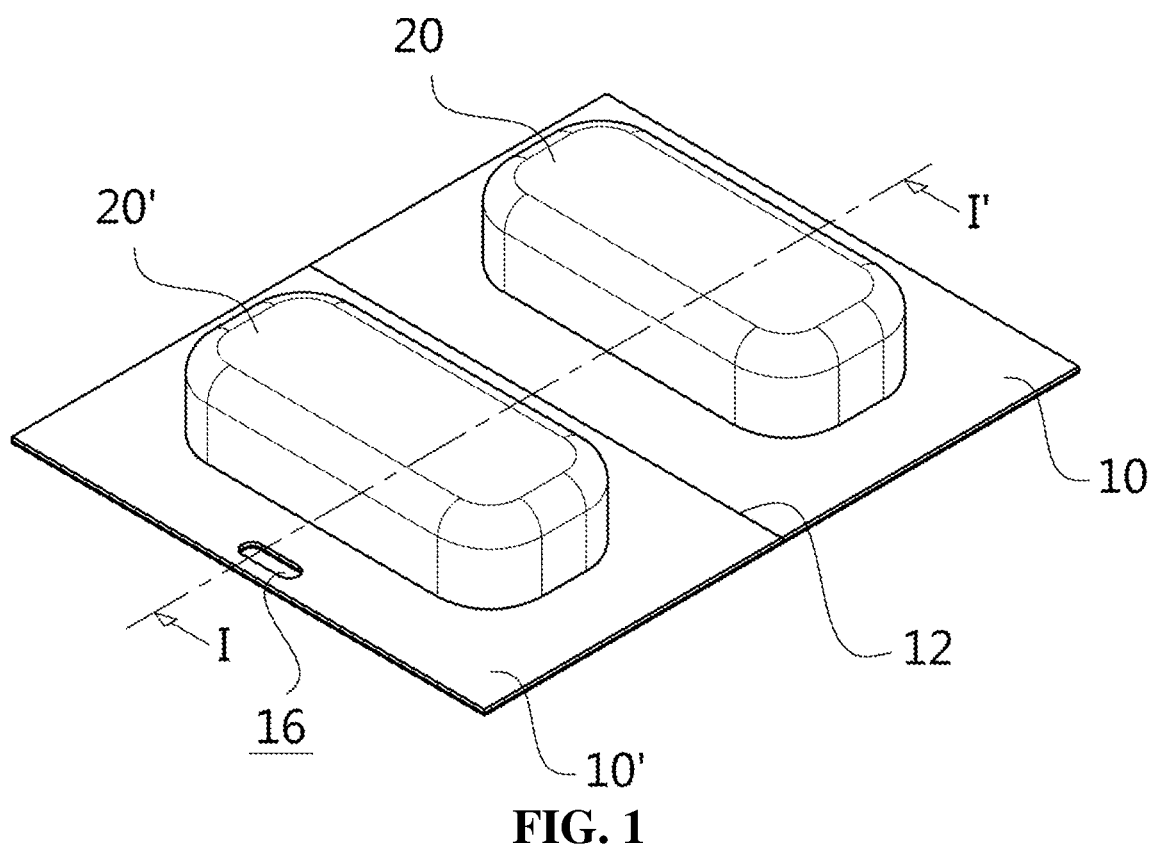
FIG. 1 is a perspective view showing a configuration of an exemplary embodiment of a medical tube holder according to the present disclosure.
Figure 2A:
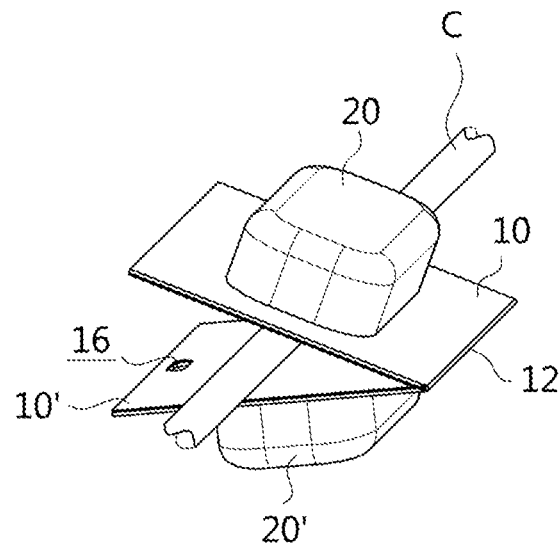
FIGS. 2(*a*) and 2(*b*) are exemplary views each showing a state in which the present disclosure is applied and used in a medical tube.
Figure 2B:
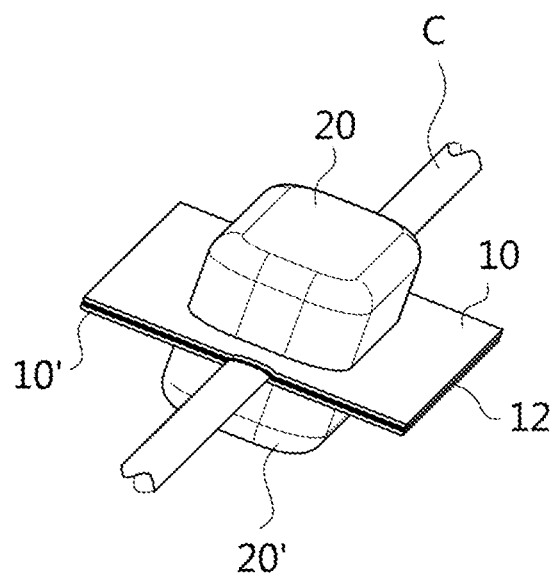

Hereinafter, some exemplary embodiments of the present disclosure will be described in detail through exemplary views. In adding reference numerals to the components of each drawing, it should be noted that the same reference numerals are used to refer to the same components as much as possible even if displayed on different drawings. Further, in the following description, if it is decided that the detailed description of a known function or configuration related to the disclosure makes the subject matter of the disclosure unclear, the detailed description is omitted.

In addition, in describing the components of the exemplary embodiments of the present disclosure, terms such as first, second, A, B, (a), (b), and the like can be used. Since these terms are provided merely for the purpose of distinguishing the components from each other, they do not limit the nature, sequence, or order of the components. If a component is described as being "connected", "coupled", or "linked" to another component, that component may be directly connected or connected to that other component, however it should be understood that yet another component between each of the components may be "connected", "coupled", or "linked" to each other.

A medical tube holder (hereinafter referred to as "tube holder") according to the present exemplary embodiment is a cylindrical member having a predetermined diameter and length that surrounds the outer circumference of a medical tube C by passing the medical tube C into the inside of the medical tube holder. This is based on an idea that it is possible to insert the medical tube without direct contact with the medical tube by enabling a user to hold the medical tube C through the tube holder.

In addition, the tube holder of the present exemplary embodiment is not limited in its use to treat a patient by using the medical tube C, and may be used, for example, to insert a known guidewire that is first inserted before inserting the medical tube.

FIG. 1 is a perspective view showing exterior appearance of a tube holder according to an exemplary embodiment of the present disclosure. As shown, in the tube holder of the present exemplary embodiment, holder bodies 10 and 10' form a framework. The holder bodies 10 and 10' have a substantially thin plate-like structure. In the present exemplary embodiment, the holder bodies 10 and 10' have a shape of the thin plate, and protruding fluid pockets 20 and 20' are provided therein. The holder bodies 10 and 10' and the fluid pockets 20 and 20' may be integrally formed of one material.

The holder bodies 10 and 10' are composed of a first body 10 and a second body 10'. The first body 10 and the second body 10' have a structure symmetrical to each other, and a folding line 12 is formed therebetween. Based on the folding line 12, the first body 10 and the second body 10' may be folded or unfolded in a direction in which the first and second bodies overlap each other. The folding line 12 is a part having a rather thin thickness between the holder bodies 10 and 10', and the first body 10 and the second body 10' may be easily folded or unfolded based on the folding line 12. The fold line 12 may be made in a form where a part thereof is penetrated by punching, or may be made into a pressed shape. Obviously, the folding line 12 may be omitted.

The holder bodies 10 and 10' may be made of various materials such as metal, plastic, PET, etc., and are preferably made of a material that may maintain a certain shape but is elastically deformable to some extent.

Since the holder bodies 10 and 10' are composed of the first body 10 and the second body 10' that may adjust an interval therebetween, the medical tube C may be positioned between the first body 10 and the second body 10'. In addition, when the first body 10 and the second body 10' are folded and the interval between the two bodies is narrowed, the holder bodies 10 and 10' surround the medical tube C positioned therebetween, and as a result, it is possible to grip the medical tube C by using the tube holder.

More precisely, the first body 10 and the second body 10' are each formed in a plate shape, and are configured to be folded in a direction overlapping each other, so as to surround the medical tube C positioned therebetween. The fluid pockets 20 and 20' to be described below may be formed on at least one side of the first body 10 or the second body 10', and have a structure of protruding toward an opposite direction of the medical tube C.

Figure 3:
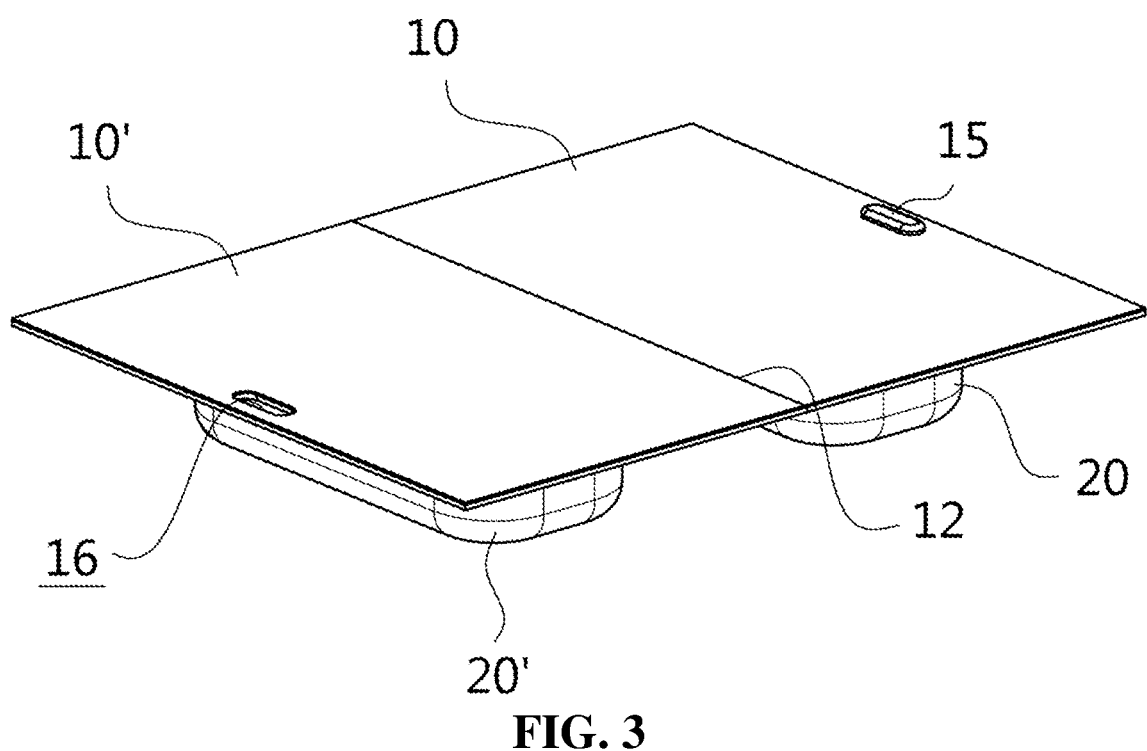
FIG. 3 is a perspective view showing a bottom configuration of the exemplary embodiment of the present disclosure shown in FIG. 1.

As shown in FIG. 3, a fixing protrusion 15 and a fixing groove 16 are formed at positions corresponding to the first body 10 and the second body 10', respectively. The fixing protrusion 15 and the fixing groove 16 serve to fix the first body 10 and the second body 10' to each other, the first and second bodies being in a folded and overlapped state. The fixing protrusion 15 may be pressed into the fixing groove 16 to maintain a fixed state.

Figure 4:
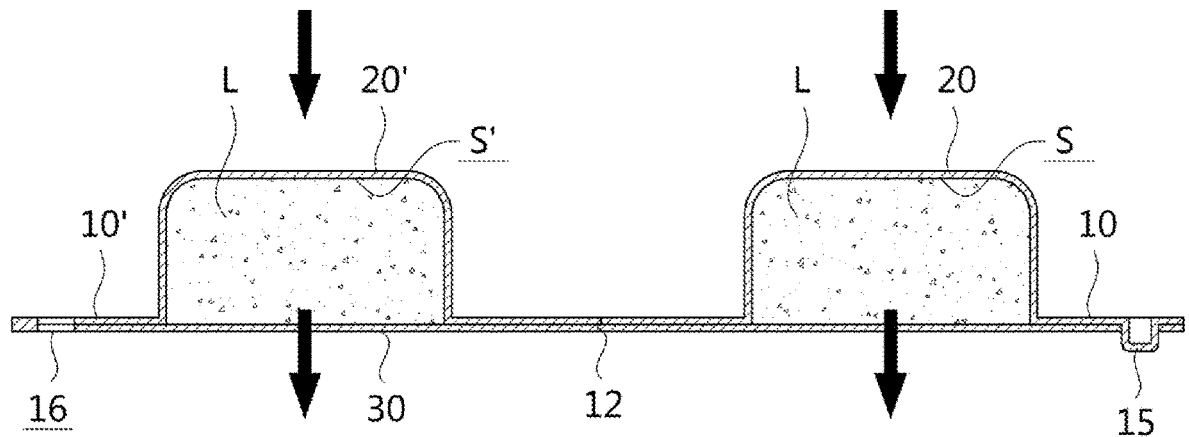
FIG. 4 is a cross-sectional view taken along line I-I' of FIG. 1.

The fluid pockets 20 and 20' are formed in the holder bodies 10 and 10', respectively. The fluid pockets 20 and 20' are respectively provided in the holder bodies 10 and 10' to form a predetermined space, and when pressed by an external force (in the direction of the upper arrow in FIG. 4), as at least a part of the fluid pockets is broken, the fluid stored therein is discharged in the outer surface direction of the medical tube C (in the direction of the lower arrow in FIG. 4). In the present exemplary embodiment, the fluid pockets 20 and 20' are integrally formed with the holder bodies 10 and 10' respectively, but obviously the fluid pockets may be made of materials different from that of the holder bodies.

The fluid pockets 20 and 20' may be made in various shapes, and as shown in FIG. 1 in the present exemplary embodiment, each fluid pocket has a dome shape protruding from each of the holder bodies 10 and 10'. The fluid pockets 20 and 20' need not be limited in shape, such as circular, elliptical, or various polygonal shapes. Preferably, the fluid pockets 20 and 20' are made of transparent materials, so that a lubricant L, which is an internal fluid, may be visually checked from the outside.

Like the holder bodies 10 and 10', the fluid pockets 20 and 20' usually maintain its shape to some extent, and may be deformed when an external force is applied. More precisely, when the external force is applied in the direction of the arrow in FIG. 4, the volume of the storage spaces S and S' is reduced as the fluid pockets are crushed downward.

The fluid pockets 20 and 20' are respectively formed by storage spaces S and S', formed in the holder bodies 10 and 10' respectively, and a sealing film 30 sealing the storage spaces S and S' and to be broken by internal pressure of the storage spaces S and S' when an external force is applied thereto. The sealing film 30 forms the lower part of the fluid pockets 20 and 20', and is in close contact with the holder bodies 10 and 10' to seal the storage spaces S and S'. The sealing film 30 is preferably made of a material that is very thin enough to be broken by the external force.

That is, the sealing film 30 is coupled to the holder bodies 10 and 10' by a kind of blister manufacturing method to seal the predetermined spaces. That is, a recessed part is made in each of the holder bodies 10 and 10' that are packaging materials having a flat surface, so as to be suitable for the shape of the fluid (i.e., lubricant L) that is an object to be packaged, whereby the packaged object is placed therein, and then the fluid pockets are made by covering the holder bodies with the sealing film 30, which is another packaging material. The sealing film 30 may be fixed to the holder bodies 10 and 10' in various ways such as use of adhesive or ultrasonic welding. In addition, the sealing film 30 may be printed with a product name, a manufacturer's name, or other information in a manner such as gravure printing and transfer printing.

The exemplary embodiment shown in FIG. 1 shows that fluid pockets 20 and 20' are respectively formed on the first body 10 and the second body 10' constituting the holder bodies 10 and 10'. However, the fluid pockets 20 and 20' may be formed only on the first body 10 or the second body 10'. In the case where the fluid pockets 20 and 20' are provided on the first body 10 and the second body 10', respectively, after using the lubricant L contained in one of the two fluid pockets 20 and 20' first, the lubricant L contained in the remaining fluid pockets 20 and 20' may be used later.

Figure 5:
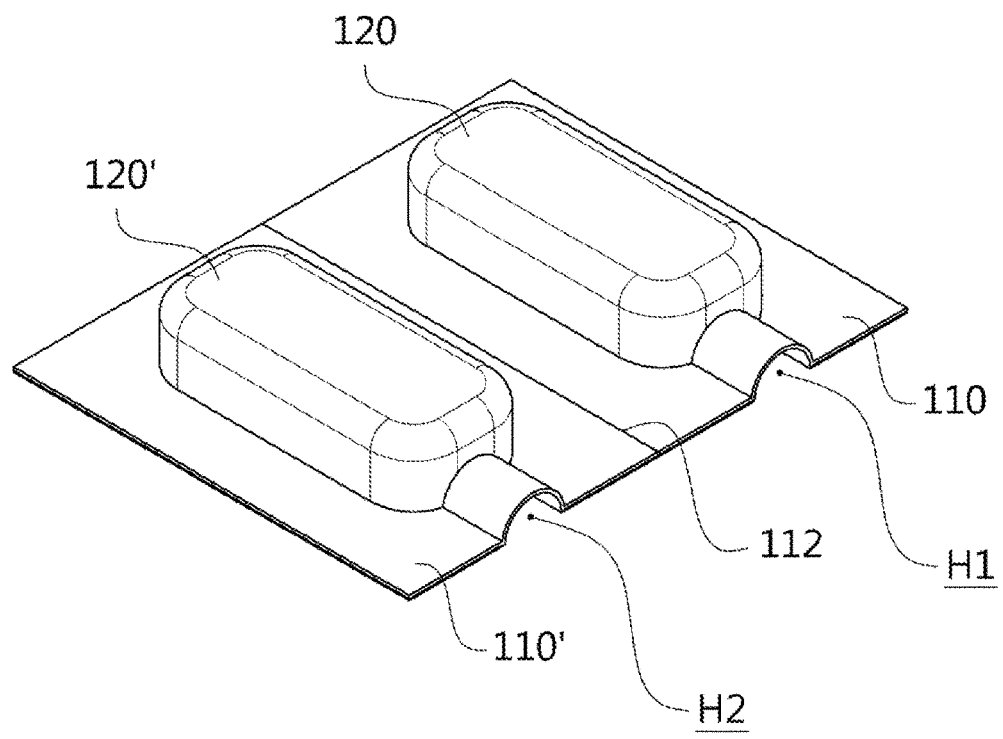
FIG. 5 is a perspective view showing a configuration of a second exemplary embodiment of a medical tube holder according to the present disclosure.

FIG. 5 is a view showing a second exemplary embodiment of a medical tube holder according to the present disclosure. The reference numerals in the 100th range are assigned to the same parts as in the previous exemplary embodiment, and detailed descriptions will be omitted.

As can be seen from the drawings, a guide groove H corresponding to the outer surface of the medical tube C is formed to be concave in each of the holder bodies 110 and 110'. The guide groove H is extended in the extending direction of the medical tube C to surround the medical tube C, and the guide groove H is formed by a bent part made of a form in which each part of the holder bodies 110 and 110' is bent.

Figure 6:
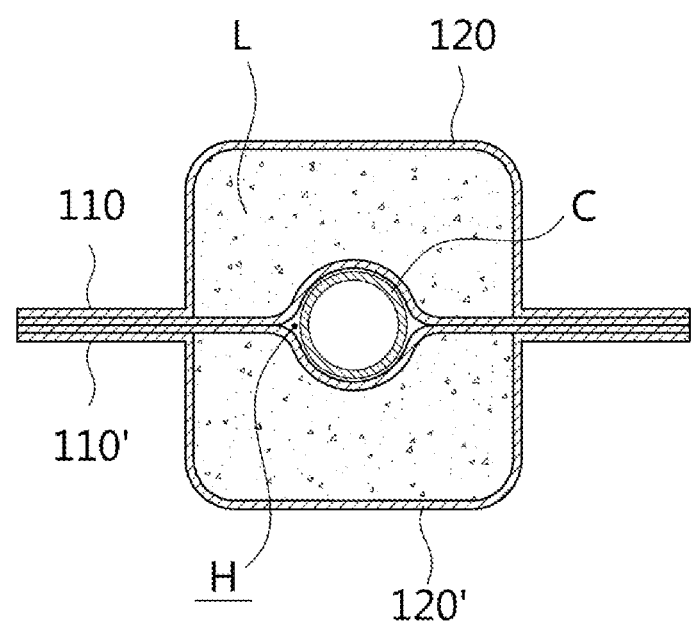
FIG. 6 is a cross-sectional view showing the structure of the exemplary embodiment shown in FIG. 5.

Guide grooves H1 and H2 are respectively formed on the first body 110 and the second body 110' constituting the holder body 110 and 110', and the two guide grooves H1 and H2 form one circular guide groove H when the first body 110 and the second body 110' are folded and overlap each other. Such a shape is shown in FIG. 6. By the guide groove H, the medical tube C is sandwiched between the holder bodies 110 and 110' and may be extended without being compressed or deformed.

Figure 7:
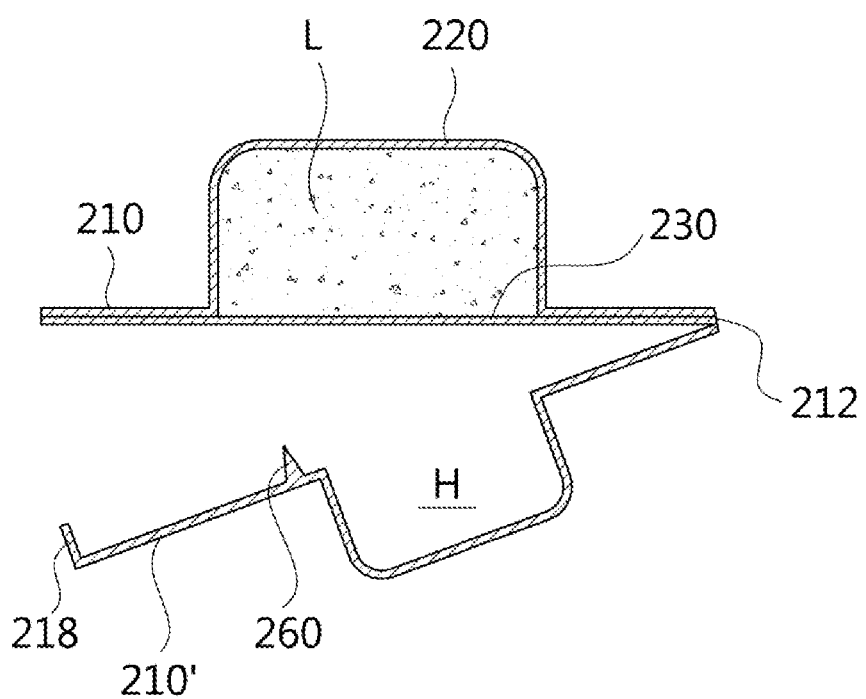
FIG. 7 is a perspective view showing a configuration of a third exemplary embodiment of a medical tube holder according to the present disclosure.

FIG. 7 is a view showing a third exemplary embodiment of a medical tube holder according to the present disclosure. The reference numerals in the 200th range are assigned to the same parts as in the previous exemplary embodiments, and detailed descriptions will be omitted.

In the exemplary embodiment shown in FIG. 7, the fluid pocket 220 is provided only on the first body 210 among the first body 210 and the second body 210' constituting the holder bodies 210 and 210'. In addition, a fracture protrusion 260 is provided on the second body 210' to protrude therefrom toward the opposite member, that is, the first body 210. The fracture protrusion 260 breaks the sealing film provided on the first body 210 in the process of contacting the first body 210 and the second body 210' with each other, thereby serving to discharge the fluid in the storage spaces S and S' more smoothly. A plurality of fracture protrusions 260 having a sharp tip structure may be provided on the second body 210'.

The holder body 210' is provided with a fixing piece 218. The fixing piece 218 may be provided on any one side of the first body 210 and the second body 210', and is provided on the second body 210' in the exemplary embodiment of FIG. 7. When the fixing piece 218 is deformed by an external force so as to surround the edge of the first body 210 in a state where the first body 210 and the second body 210' are folded and overlapped each other, the first body 210 and the second body 210' are allowed to be able to maintain the overlapped state.

Figure 8:
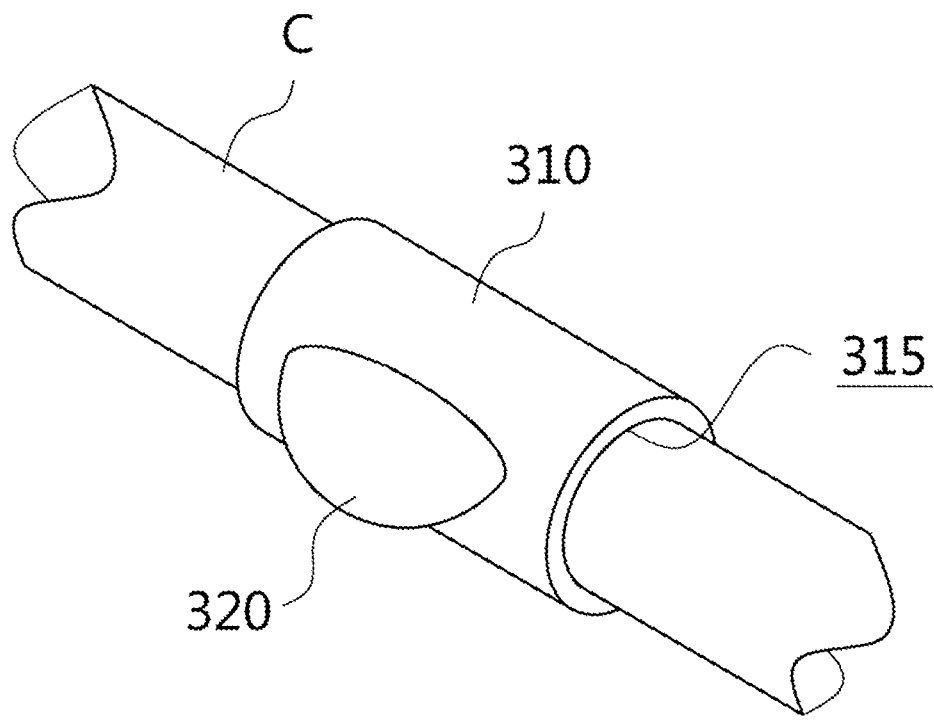
FIG. 8 is a perspective view showing a configuration of a fourth exemplary embodiment of a medical tube holder according to the present disclosure.

FIG. 8 is a view showing a fourth exemplary embodiment of a medical tube holder according to the present disclosure. In this exemplary embodiment, the medical tube holder has a holder body 310 having a cylindrical shape, and a through hole 315 through which the medical tube C passes is formed in the holder body 310. The through hole 315 has a circular cross section to correspond to the medical tube C.

The tube holder has an elastic restoring force, so that when the outer circumferential surface thereof is pressed by hand before the pressed force is removed, the original state of the tube holder is restored. That is, when a force is applied to the tube holder in the direction of the medical tube C, the tube holder is pressed inward and the outer circumferential surface of the medical tube C inserted therein is pressed as well and tightened, and when the applied force is removed, the original cylindrical shape of the tube holder is restored.

At this time, the fluid pocket 320 is formed on the outer surface of the holder body 310. That is, the fluid pocket 320 has a structure of protruding toward the outside of the holder body 310, and a lubricant L, which is a fluid, is contained in the fluid pocket. Accordingly, when a user grips the holder body 310 strongly, a part of the fluid pocket 320 is torn, and the lubricant L is discharged to the outside and applied to the outer surface of the medical tube C.

Although not shown, a sealing film for sealing the fluid pocket 320 is attached to the inner circumferential surface of the holder body 310, and the holder body has a structure in which when the sealing film is broken, the lubricant L inside the fluid pocket 320 is discharged to the outside.

Figure 9:
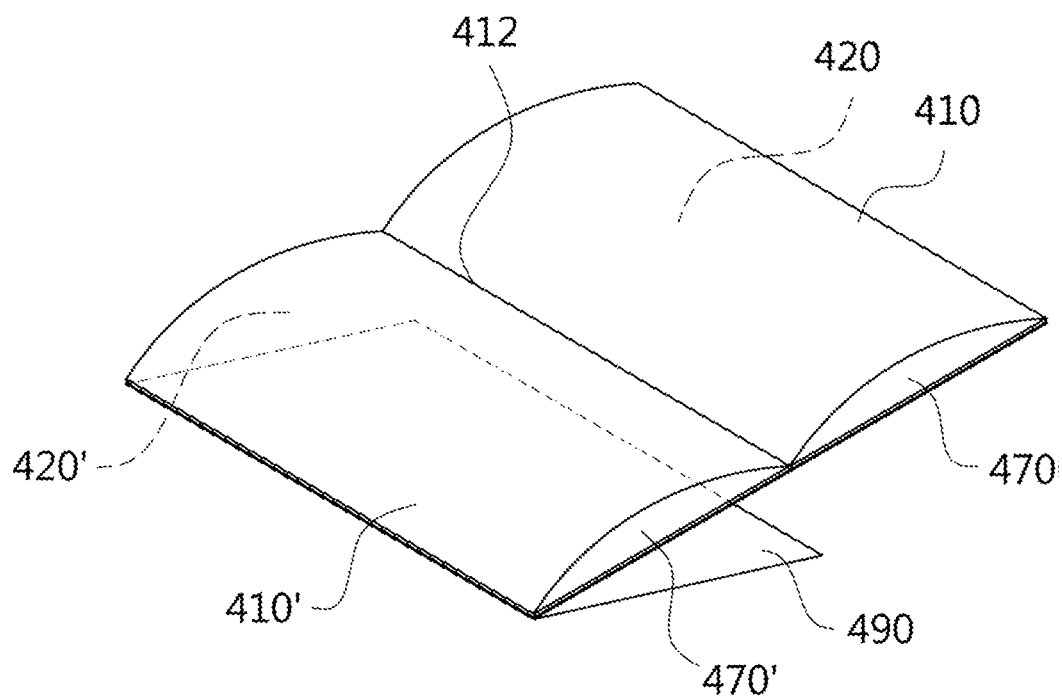
FIG. 9 is a perspective view showing a configuration of a fifth exemplary embodiment of a medical tube holder according to the present disclosure.

FIG. 9 is a view showing a fifth exemplary embodiment of a medical tube holder according to the present disclosure. As can be seen, in the tube holder of the present exemplary embodiment, at least a part of the outer surfaces of the holder bodies 410 and 410' may be formed in a streamlined shape as a whole. When having such a shape, the tube holder has an advantage of fixing the tube of more various standards thereto without a gap, and since the surface in contact with the outer surface of the tube has a curved shape, the fluid may be more evenly applied to the outer surface of the tube.

In FIG. 9, the upper parts of the holder bodies 410 and 410' are shown in a streamlined manner, but each of the bottom surfaces of the holder bodies 410 and 410' may also have a streamlined shape. In the present exemplary embodiment, each of the fluid pockets 420 and 420' also have a streamlined shape. In the exemplary embodiment, the fluid contained in fluid pockets 420 and 420' may be discharged through outlets 470 and 470' formed in front of each of the fluid pockets 420 and 420', respectively. Reference numeral 490 denotes a cover, and the cover 490 is folded over the two holder bodies 410 and 410', which are in a state of being overlapped with each other. The cover 490 may surround the upper part of the tube holder to prevent the fluid stored therein from flowing out, or may store the fluid between the cover 490 and the holder bodies 410 and 410'.

Figure 10:
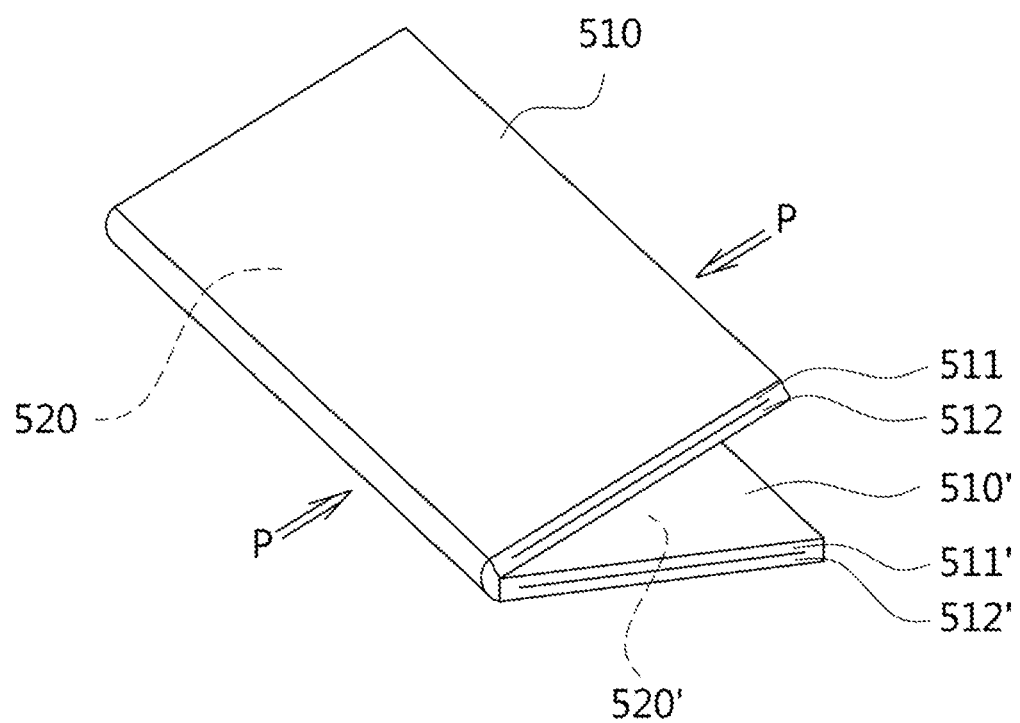
FIG. 10 is a perspective view showing a configuration of a sixth exemplary embodiment of a medical tube holder according to the present disclosure.

FIG. 10 is a view showing a sixth exemplary embodiment of a medical tube holder according to the present disclosure. As can be seen, in the tube holder, the holder bodies 510 and 510' may be made of a semi-soft material, for example, a vinyl material of two thin layers 511 and 512, and 511' and 512'. In addition, a fluid pocket 520 is formed between the outer surfaces of the two layers 511 and 512, and 511' and 512'. The fluid contained in such a fluid pocket 520 is discharged to the outside through an outlet formed between the two layers of semi-soft materials 511 and 512, and the two layers of semi-soft materials 511' and 512', so as to coat the outer surface of the tube.

In the present exemplary embodiment, when an external force is applied from opposite sides of each of the holder bodies 510 and 510' (refer to the P direction in FIG. 10), as the outlet of the holder bodies 510 and 510' composed of the two layers 511 and 512, and 511' and 512' respectively is opened, the fluid inside the fluid pocket is discharged to the outside. At this time, when an external force is applied to the fluid pocket 520, due to an increased internal pressure, the fluid may be discharged from the fluid pocket 520 through the outlet.

According to the present exemplary embodiment, tubes having various sizes may be applied to the holder bodies 510 and 510' of soft materials, and the holder bodies 510 and 510' are more closely in contact with the outer surface of the tube, thereby improving the usability. In addition, a separate fluid may be spread inside of the two holder bodies 510 and 510' and utilized.

Although not shown, each outlet of the fluid pocket 520 is formed between the two-layer materials 511 and 512, and the two-layer materials 511' and 512', and a jaw structure may be formed at the edge of each outlet, or a rib structure may be formed on first layers 511 and 511' and a groove structure corresponding to the rib structure may be formed on second layers 512 and 512', so as to be coupled to each other through an uneven structure. This is to prevent the fluid inside the fluid pocket 520 from being randomly discharged.

Next, a process of using the exemplary embodiment of the present disclosure shown in FIG. 1 will be described.

The tube holder is coupled to the outer circumferential surface of the medical tube C, so that the user may handle the medical tube C by gripping the tube holder without directly gripping the medical tube C.

To describe a process of inserting the tube holder into the medical tube C, first, the medical tube C is placed between the first body 10 and the second body 10' each constituting the holder bodies 10 and 10' of the tube holder, and when the first body 10 and the second body 10' are folded in the direction in which the first body 10 and the second body 10' are overlapped with each other, the medical tube C is inserted between the first body 10 and the second body 10'. Accordingly, the user may handle the medical tube C by gripping the tube holder without directly gripping the medical tube C.

At this time, since the fixing protrusion 15 and the fixing groove 16 are formed at positions corresponding to each other in the first body 10 and the second body 10', in the process of overlapping the first body 10 and the second body 10', the fixing protrusion 15 is press-fit into the fixing groove 16 to maintain a fixed state of the first body 10 and the second body 10'.

As described above, in the present disclosure, since the first body 10 and the second body 10' may be separated from each other or overlapped with each other, the medical tube C having various shapes and sizes may be positioned therebetween, so that a single tube holder may be applicable for various medical tubes C.

Meanwhile, in this fixed state, when an external force is applied in the direction in which the first body 10 and the second body 10' are further closely contacted with each other, the fluid pockets 20 and 20' are pressed and crushed, whereby internal pressure of the storage spaces S and S' increases. When the internal pressure of the storage spaces S and S' exceeds a certain level, the sealing film 30 is broken and the lubricant L stored in the storage spaces S and S' is discharged so as to be applied to the outer surface of the medical tube C.

Subsequently, when the tube holder is moved along the outer surface of the medical tube C, while spreading evenly on the outer surface of the tube, the lubricant L may be applied to the outer surface of the tube. In this way, the lubricant L is stored in the tube holder of the present disclosure, and the stored lubricant L may be applied to the outer circumferential surface of the medical tube C during use of the tube holder. Accordingly, the user may easily apply the lubricant L by using the tube holder, and a separate work for applying the lubricant L is unnecessary.

In addition, since the user may visually confirm that the lubricant L is applied while the fluid pockets 20 and 20' are deformed, more accurate use is possible.

Meanwhile, the work of applying the lubricant L may be performed in another way. For example, instead of pressing the fluid pockets 20 and 20', the first body 10 constituting the holder bodies 10 and 10' itself may be broken, so that the sealing film 30 may also be broken in the process of the breakage. At this time, by forming a predetermined breaking line (not shown) on the sealing film 30 in advance, such work may be made more easily.

In the description above, although the components of the exemplary embodiments of the present disclosure may have been explained as assembled or operatively connected to each other as a unit, the present disclosure is not intended to limit itself to such exemplary embodiments. That is, within the scope of the present disclosure, all of the components may be selectively combined and operated in any numbers. In addition, the terms "comprise", "include", or "have" described above mean that the corresponding component may be inherent unless otherwise stated, and thus it should be construed that it may further include other components, not to exclude other components. That is, terms like "include", "comprise", and "have" should be interpreted in default as inclusive or open rather than exclusive or closed unless expressly defined to the contrary. In the following description, unless otherwise defined, all terms including technical and scientific terms used herein have the same meaning as commonly understood by one of those skilled in the art to which this disclosure belongs. Commonly used terms, such as predefined terms, should be interpreted as being consistent with the contextual meaning of the related art, and are not to be interpreted as ideal or excessively formal meanings unless explicitly defined in the present disclosure.

Although exemplary aspects of the present disclosure have been described for illustrative purposes, those skilled in the art will appreciate that various modifications, additions and substitutions are possible, without departing from essential characteristics of the disclosure. Therefore, the embodiments disclosed in the present disclosure are not intended to limit the technical idea of the present disclosure but to describe the present disclosure, and the scope of the technical idea of the present disclosure is not limited by these embodiments. The scope of protection of the present disclosure should be interpreted by the following claims, and all technical ideas within the scope equivalent thereto should be construed as being included in the scope of the present disclosure.

The invention claimed is:

1. A medical tube holder comprising:
a holder body configured to be folded for surrounding an outer surface of a medical tube; and
a fluid pocket disposed on the holder body, the fluid pocket forming a storage space and being configured for discharging fluid stored therein to the outer surface of the medical tube by increased internal pressure when pressed by an external force,
wherein the holder body includes a first body and a second body separated from the first body by an interval,
wherein the medical tube is positioned between the first body and the second body, and a distance of the interval is adjusted when the holder body is folded,
wherein the fluid pocket protrudes outward from one surface of the holder body, and another surface of the holder body opposite to the one surface is in contact with the medical tube when the holder body is folded, and
wherein the another surface of the holder body is opened so as for the fluid to be discharged when the fluid pocket is pressed in a direction toward the another surface of the holder body by the external force,
wherein the fluid pocket comprises:
the storage space formed on the holder body; and
a sealing film sealing the storage space and being configured to be broken by the increased internal pressure of the storage space when the external force is applied to the storage space.

2. The medical tube holder of claim 1, wherein the holder body has a thin plate shape.

3. The medical tube holder of claim 1, wherein each of the first body and the second body of the holder body has a plate shape and is configured to be folded in a direction overlapping each other to surround the medical tube positioned therebetween.

4. The medical tube holder of claim 3, wherein the first body and the second body respectively include a fixing protrusion and a fixing groove formed at positions corresponding to each other to fix the first body and the second body in a folded and overlapped state to each other.

5. A medical tube holder comprising:
a holder body configured to be folded for surrounding an outer surface of a medical tube; and
a fluid pocket disposed on the holder body, the fluid pocket forming a storage space and being configured for discharging fluid stored therein to the outer surface of the medical tube by increased internal pressure when pressed by an external force,
wherein the holder body includes a first body and a second body separated from the first body by an interval,
wherein the medical tube is positioned between the first body and the second body, and a distance of the interval is adjusted when the holder body is folded,
wherein the fluid pocket protrudes outward from one surface of the holder body, and another surface of the holder body opposite to the one surface is in contact with the medical tube when the holder body is folded, and
wherein the another surface of the holder body is opened so as for the fluid to be discharged when the fluid pocket is pressed in a direction toward the another surface of the holder body by the external force,
wherein the fluid pocket is formed in the holder body, the holder body having two layers, and an outlet is formed on a first side of the fluid pocket to be selectively opened, such that, when the external force is applied to the fluid pocket, the fluid is discharged from the fluid pocket through the outlet by the increased internal pressure.

6. A medical tube holder comprising:
a holder body configured to be folded for surrounding an outer surface of a medical tube; and
a fluid pocket disposed on the holder body, the fluid pocket forming a storage space and being configured for discharging fluid stored therein to the outer surface of the medical tube by increased internal pressure when pressed by an external force,
wherein the holder body includes a first body and a second body separated from the first body by an interval,
wherein the medical tube is positioned between the first body and the second body, and a distance of the interval is adjusted when the holder body is folded, wherein the fluid pocket protrudes outward from one surface of the holder body, and another surface of the holder body opposite to the one surface is in contact with the medical tube when the holder body is folded, and wherein the holder body has a fracture protrusion protruding from the another surface, such that the fracture protrusion is directed toward the fluid pocket when the holder body is folded to break a sealing film of the fluid pocket so as for the fluid in the storage space to be discharged from the storage space.

7. The medical tube holder of claim 6, wherein a guide groove is formed on the holder body, and the guide groove extends from the fluid pocket in a direction that the medical tube is arranged such that the guide groove surrounds the medical tube when the holder body is folded.

\* \* \* \* \*